United States Patent [19]

Goldenberg

[11] Patent Number: 5,188,632
[45] Date of Patent: Feb. 23, 1993

[54] GUIDANCE AND DELIVERY SYSTEM FOR HIGH-ENERGY PULSED LASER LIGHT

[75] Inventor: Tsvi Goldenberg, Irvine, Calif.

[73] Assignee: Advanced Interventional Systems, Inc., Irvine, Calif.

[21] Appl. No.: 593,485

[22] Filed: Oct. 3, 1990

Related U.S. Application Data

[63] Continuation of Ser. No. 218,907, Jul. 14, 1988, abandoned, which is a continuation-in-part of Ser. No. 51,382, May 19, 1987, Pat. No. 4,830,460, which is a continuation-in-part of Ser. No. 860,241, May 6, 1986, Pat. No. 4,799,754, which is a continuation-in-part of Ser. No. 779,844, Sep. 25, 1985, Pat. No. 4,732,448, which is a continuation-in-part of Ser. No. 679,538, Dec. 7, 1984, Pat. No. 4,641,912.

[51] Int. Cl.$^5$ .............................. A61M 5/06
[52] U.S. Cl. ........................... 606/7; 606/15; 606/17; 128/397; 385/142; 385/144
[58] Field of Search ................ 606/7, 13-17; 128/395, 397, 398, 6; 385/142, 144

[56] References Cited

U.S. PATENT DOCUMENTS

| | | | |
|---|---|---|---|
| 3,327,712 | 6/1967 | Kaufman et al. | 128/398 |
| 4,009,382 | 2/1977 | Nath . | |
| 4,173,392 | 11/1979 | Ekinaka et al. | 128/6 |
| 4,270,845 | 6/1981 | Takizawa et al. . | |
| 4,272,156 | 6/1981 | Ishibashi et al. . | |
| 4,273,109 | 6/1981 | Enderly | 606/15 |
| 4,345,212 | 8/1982 | Seppala et al. | 372/92 |
| 4,398,790 | 8/1983 | Righini et al. . | |
| 4,445,754 | 5/1984 | Beaks et al. | 65/3.11 |
| 4,445,892 | 5/1984 | Hussein et al. | 606/7 |
| 4,490,020 | 12/1984 | Sakaguchi et al. . | |
| 4,521,070 | 6/1985 | Sottini et al. . | |
| 4,565,197 | 1/1986 | Daly . | |
| 4,569,335 | 2/1986 | Tsuno . | |
| 4,627,436 | 12/1986 | Leckrone | 606/7 |
| 4,641,650 | 2/1987 | Mok | 128/303.1 |
| 4,646,737 | 3/1987 | Hussein et al. | 606/28 |
| 4,672,961 | 6/1987 | Davies . | |
| 4,681,104 | 7/1987 | Edelman | 606/15 |
| 4,682,594 | 7/1987 | Mok | 128/303.1 |
| 4,686,979 | 8/1987 | Gruen et al. | 606/7 |
| 4,732,448 | 3/1988 | Goldenberg | 604/21 |
| 4,819,632 | 4/1989 | Davies . | |
| 4,830,460 | 5/1989 | Goldenberg . | |
| 4,832,023 | 5/1989 | Murphy-Chutorian et al. | 128/303.1 |
| 4,850,351 | 7/1989 | Herman et al. | 606/7 |

FOREIGN PATENT DOCUMENTS

| | | |
|---|---|---|
| 153847 | 9/1985 | European Pat. Off. . |
| 59-111125 | 1/1984 | Japan . |
| 1042281 | 2/1965 | United Kingdom . |
| 0214712 | 3/1989 | United Kingdom ..... 606/7 |

OTHER PUBLICATIONS

Lasers in Surgery and Medicine, vol. 4, Issued Jul. 25, 1984, "Far-Ultraviolet Laser Ablation of Atherosclerotic Lesions".

"Excimer Laser Surgery of the Cornea" by Truhel et al; Am J. Ophthalmology vol. 96, pp. 710-715, 1983.

"IBMs Heatless Laser Etching: A Hot IC & Medical Prospect" News Spectra Jul. 1983.

Primary Examiner—David M. Shay
Attorney, Agent, or Firm—Burns, Doane, Swecker & Mathis

[57] ABSTRACT

A fiber-optic waveguide, used for ablating lesions in blood vessels, is mounted within and guided by a catheter having multiple lumens extending therethrough and parallel to each other. The waveguide fits within at least one lumen and a guidewire, previously inserted in a blood vessel, extends through another lumen. The distal end of the waveguide can have a short section of larger diameter fiber fused to it to cause a laser beam transmitted through said fiber to expand as it emerges from the waveguide to provide a larger ablation area. The waveguide may also be connected to an energy source by means of an energy coupler. One or more balloons may be mounted to the distal end of the catheter in order to facilitate positioning the waveguide.

38 Claims, 11 Drawing Sheets

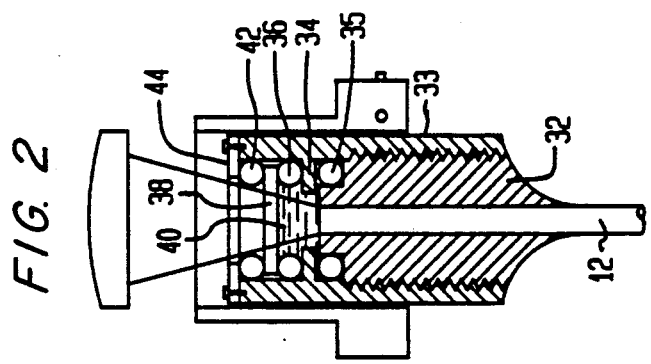
FIG. 2
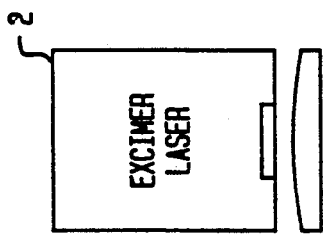
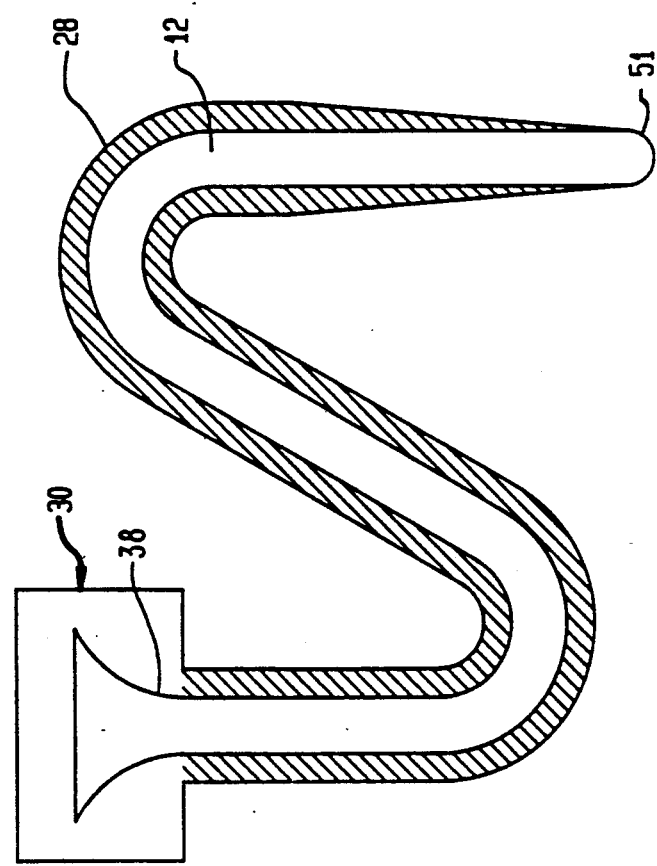
FIG. 1

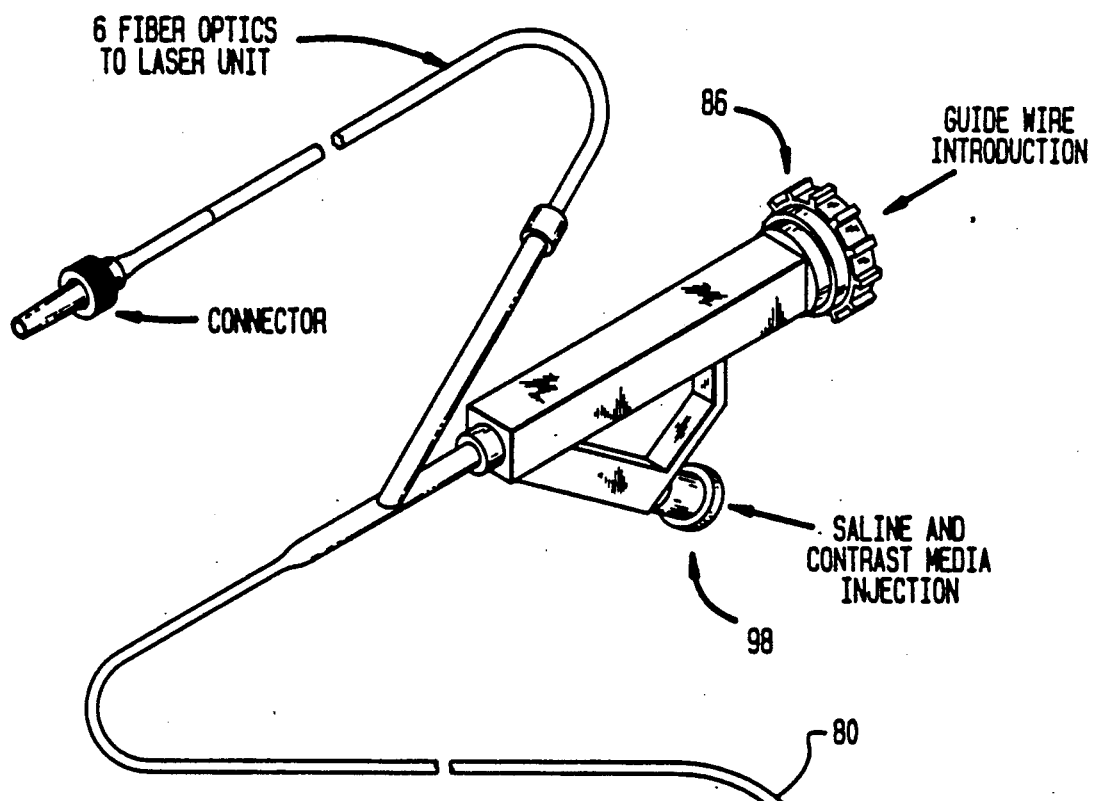
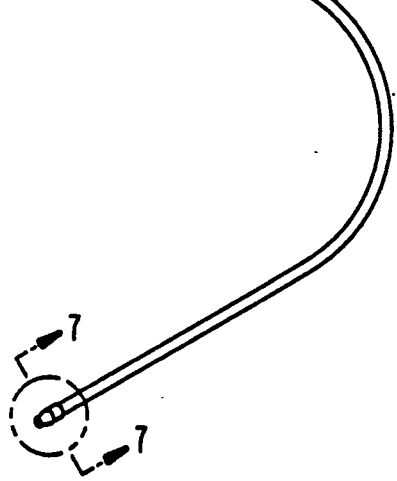
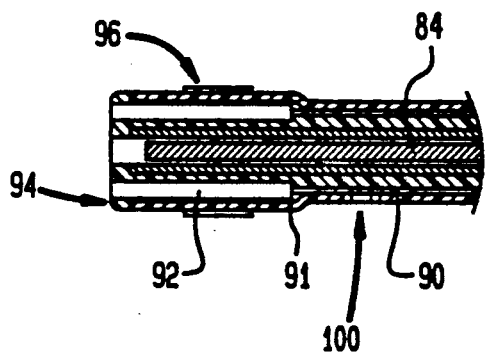
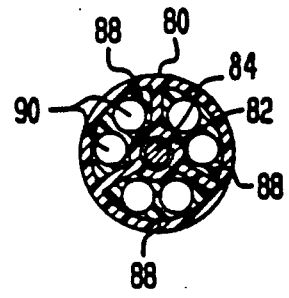
FIG. 5
FIG. 7
FIG. 6

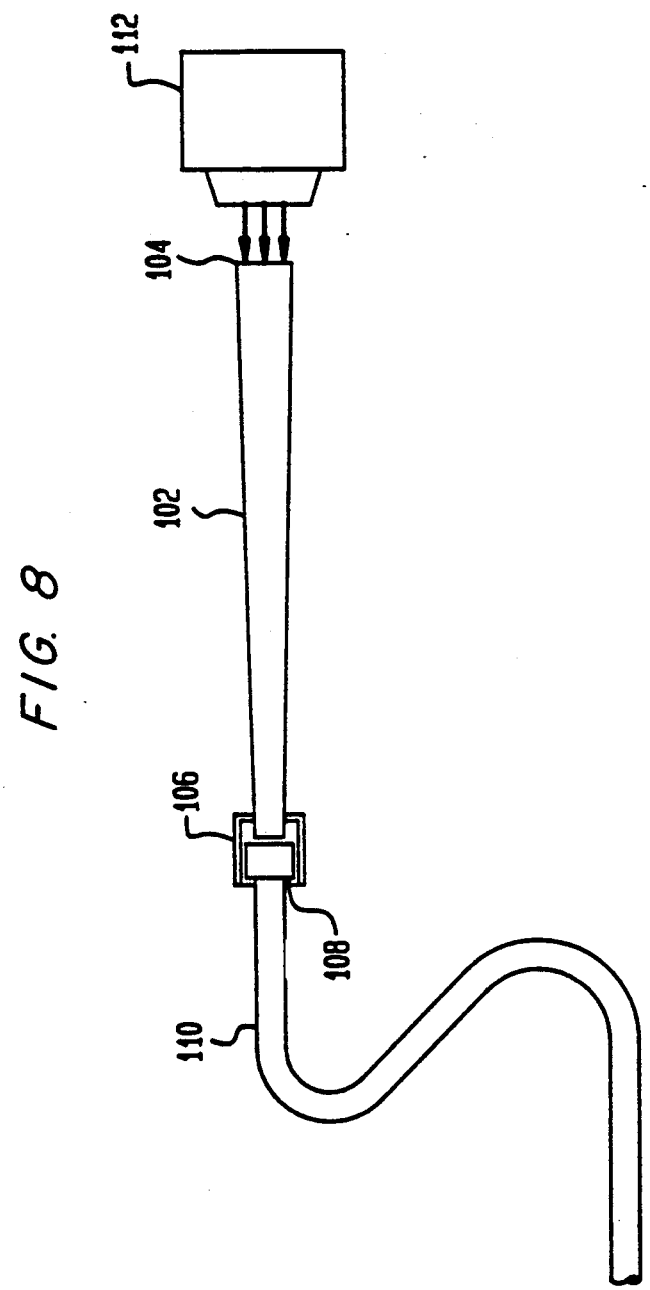

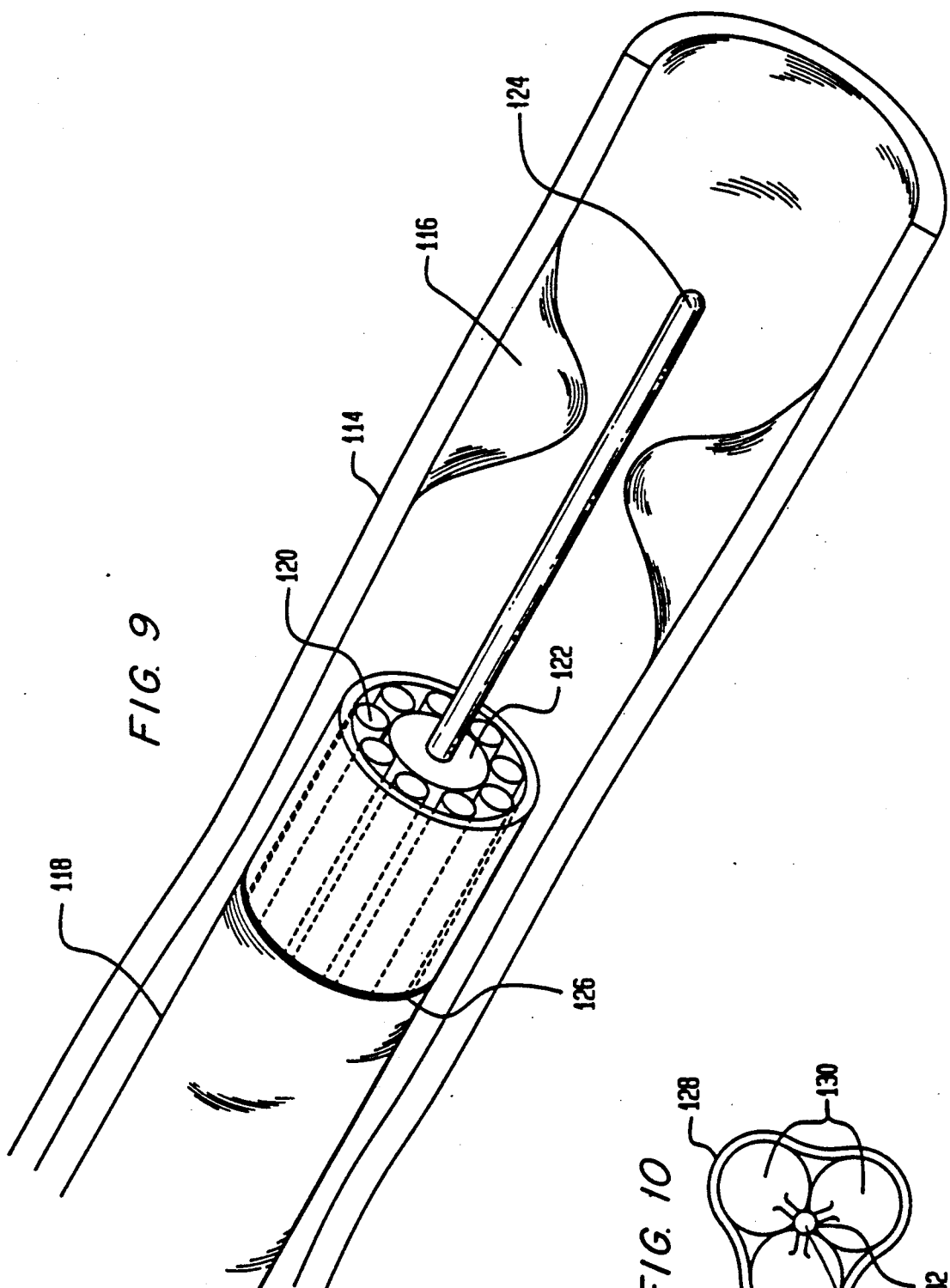

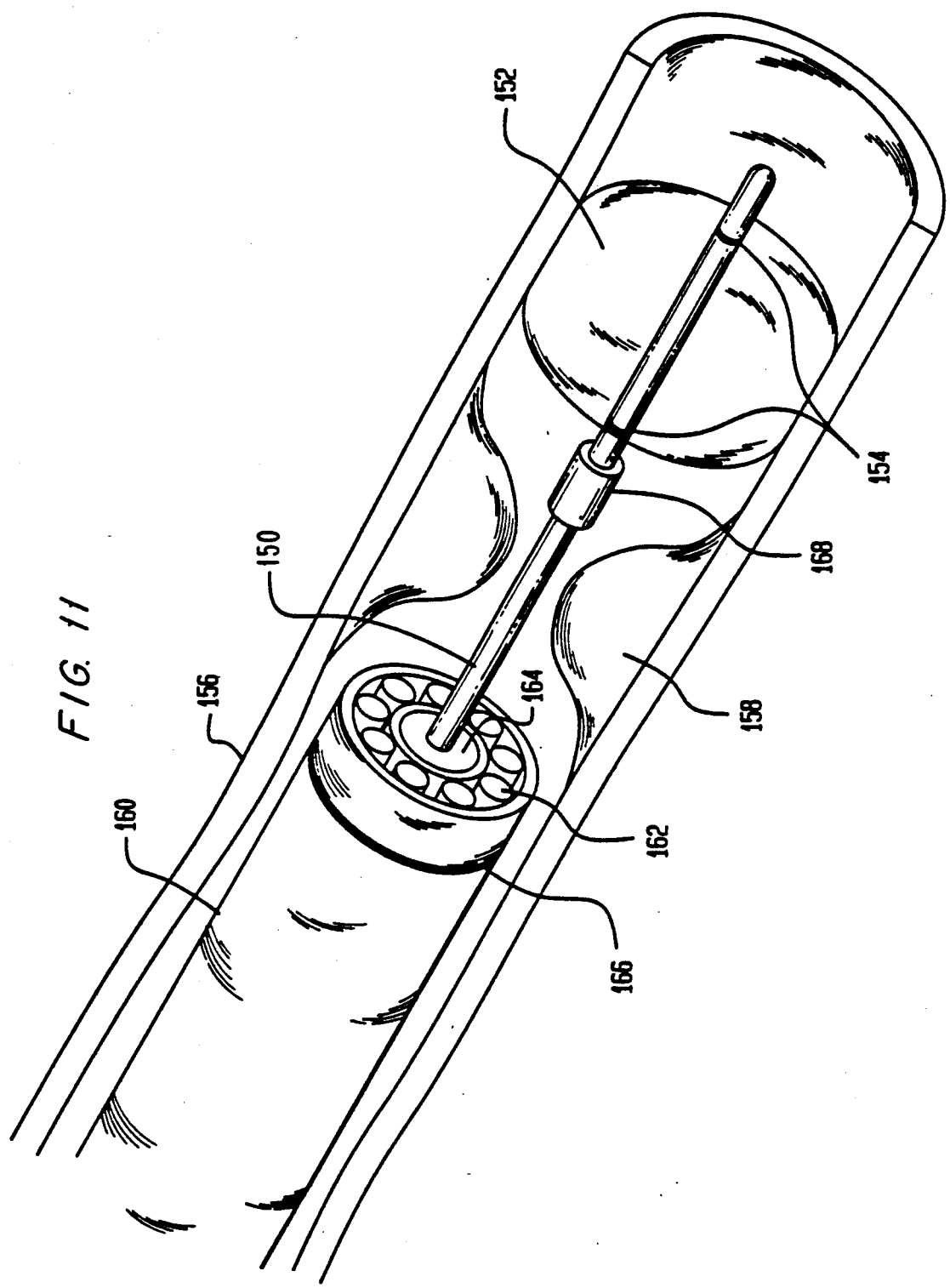

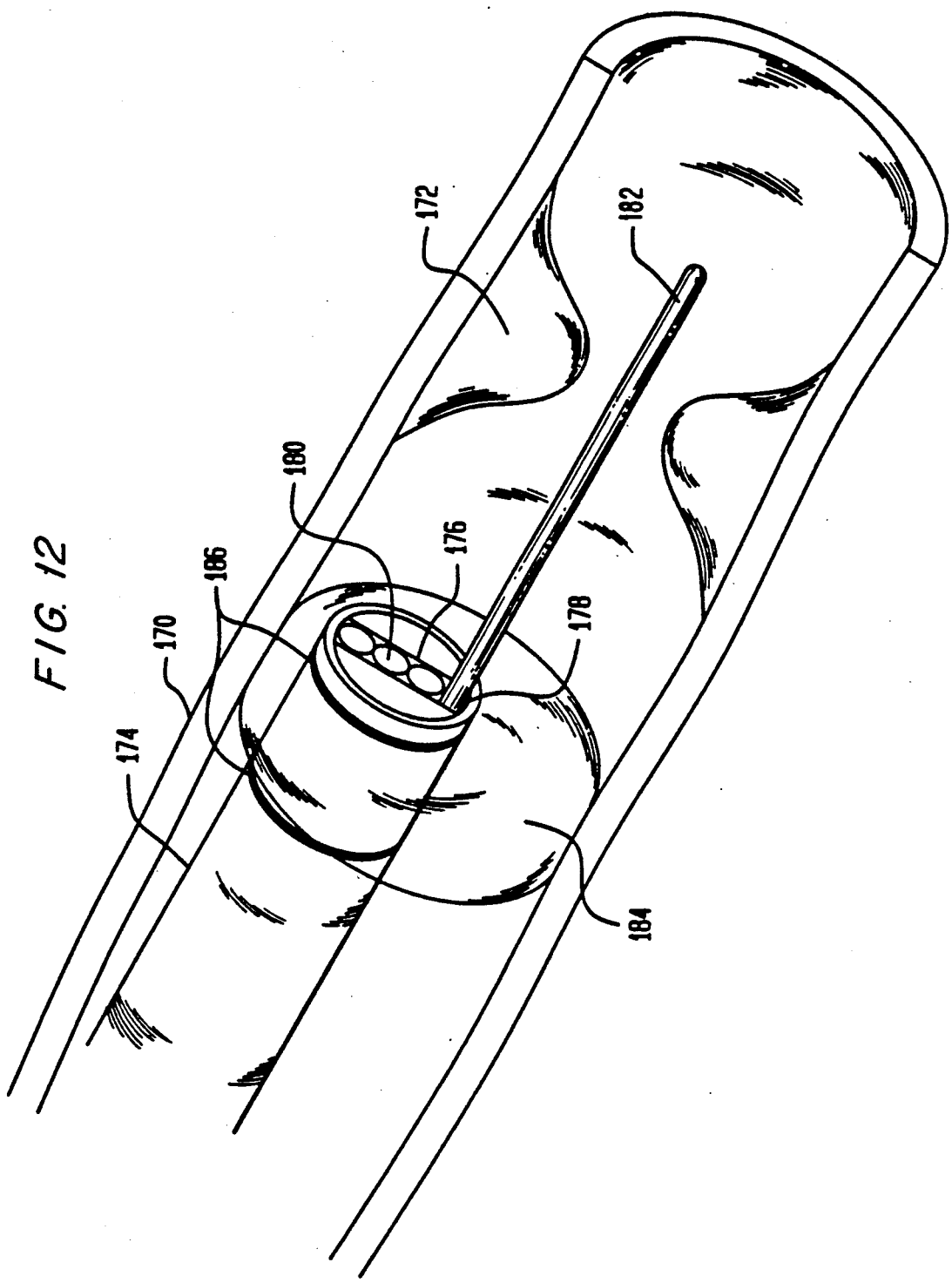

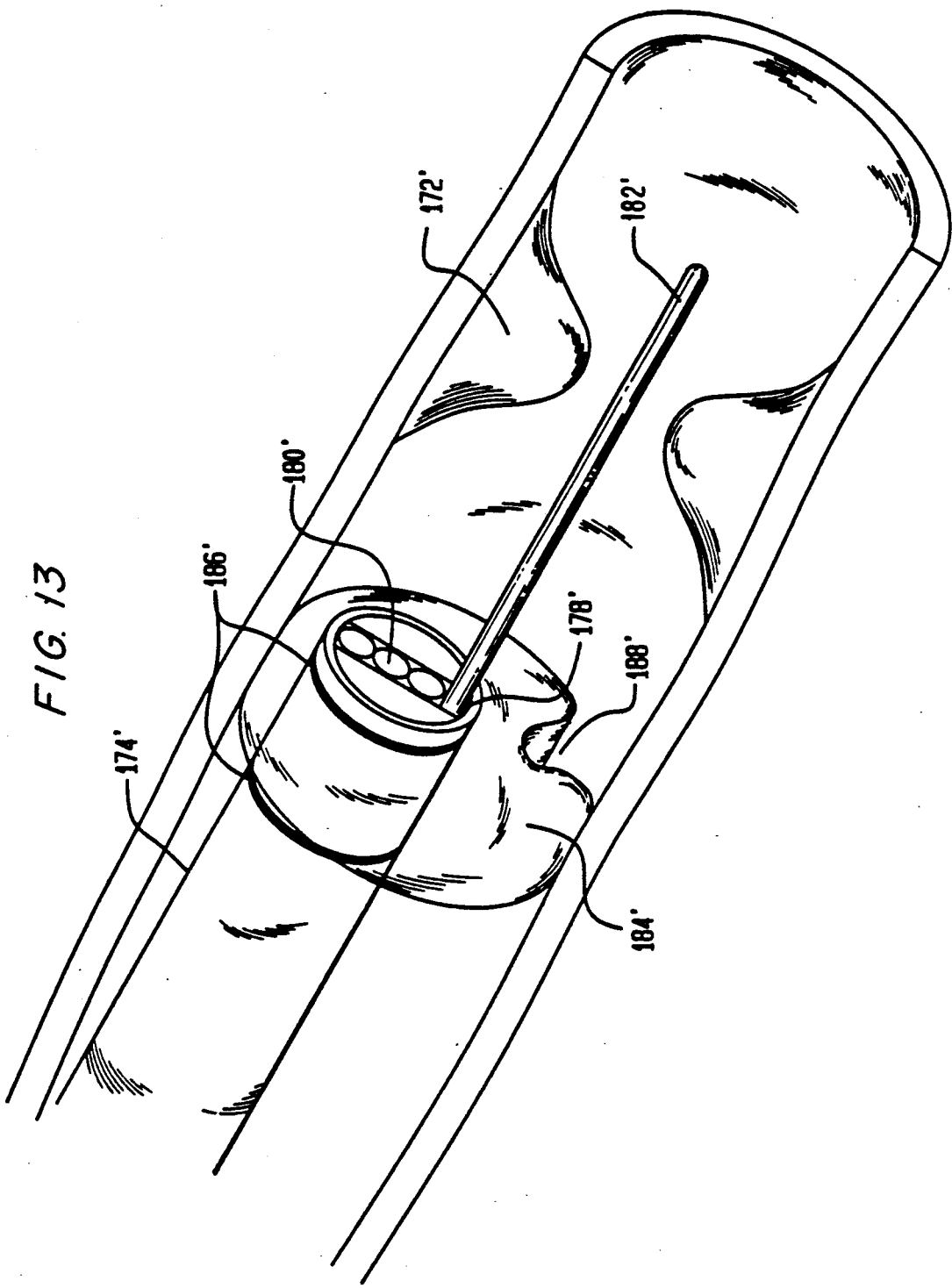

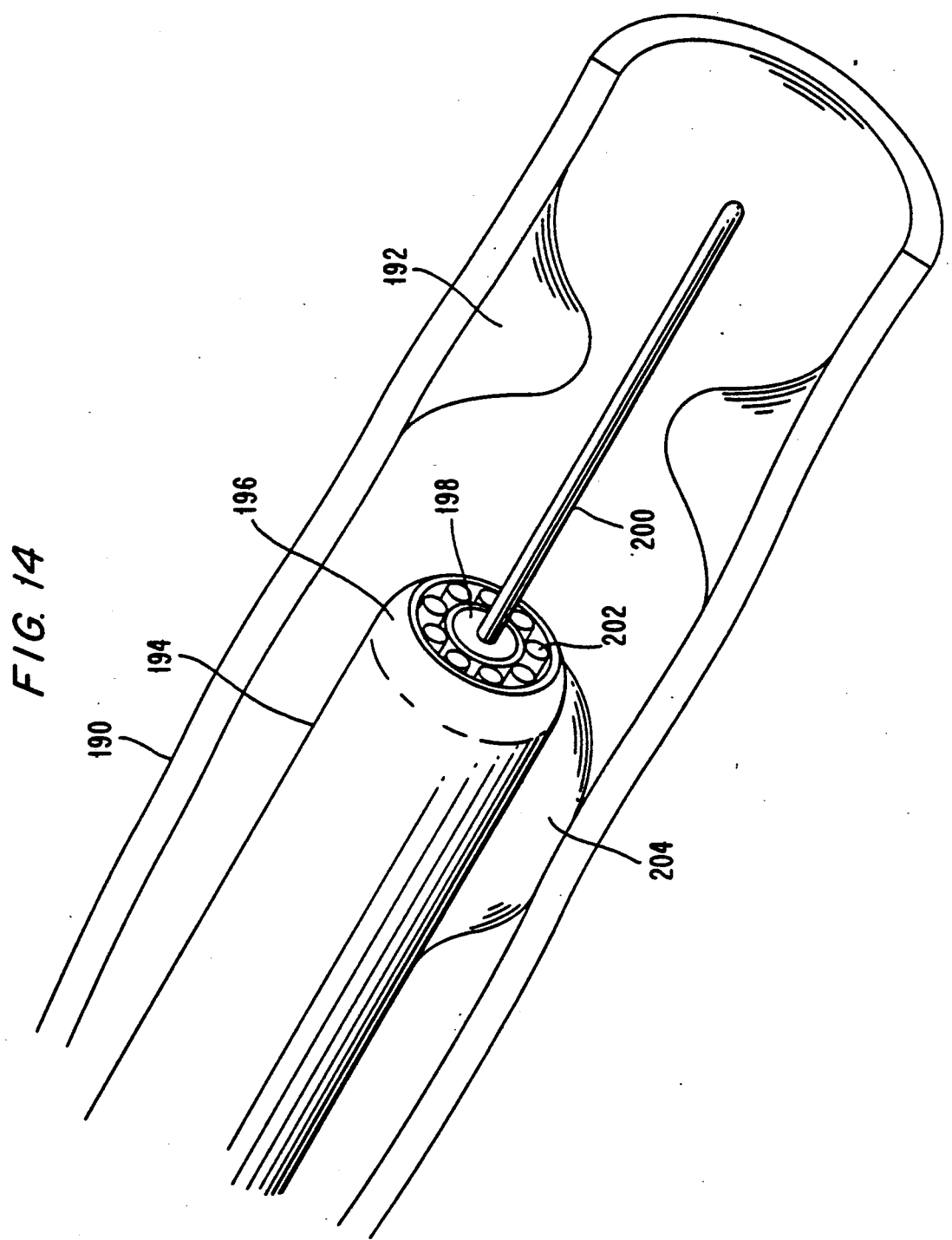

GUIDANCE AND DELIVERY SYSTEM FOR HIGH-ENERGY PULSED LASER LIGHT

CROSS REFERENCE TO RELATED APPLICATIONS

This application is a continuation of application Ser. No. 218,907, filed Jul. 14, 1988 now abandoned which is a continuation-in-part of application Ser. No. 051,382 filed May 19, 1987, now U.S. Pat. No. 4,830,460, which is itself a continuation-in-part of the Ser. No. 860,241 filed May 6, 1986, now U.S. Pat. No. 4,799,754, which is a continuation-in-part of Ser. No. 779,844 filed Sep. 25, 1985, now U.S. Pat. No. 4,732,448, which is a continuation-in-part of Ser. No. 679,538 filed Dec. 7, 1984, now U.S. Pat. No. 4,641,912, the disclosures of which are herein incorporated by reference thereto.

BACKGROUND OF THE INVENTION

The present invention is directed to a system for delivering high energy laser light by means of an optical waveguide, and in one particular application is concerned with laser angioplasty and a means for guiding such a system.

The use of laser energy to ablate atherosclerotic plaque that forms an obstruction in a blood vessel is presently being investigated as a viable alternative to coronary bypass surgery. This procedure, known as angioplasty, essentially involves insertion of a fiberoptic waveguide into the vessel, and conduction of laser energy through the waveguide to direct it at the plaque once the distal end of the waveguide is positioned adjacent the obstruction. In certain embodiments, to enable the physician to ascertain the location of the waveguide as it is being moved through the vessel, additional waveguides for providing a source of illuminating light and for conducting the image from inside the vessel to the physician are fed together with the laser waveguide.

Most of the experimentation and testing that has been done in this area has utilized continuous wave laser energy, such as that produced by Argon Ion, Nd:YAG or Carbon Dioxide lasers. The light produced by this type of laser is at a relatively low energy level. Ablation of the obstruction is achieved with these types of lasers by heating the plaque with constant laser power over a period of time until the temperature is great enough to destroy it.

While the use of continuous wave laser energy has been found to be sufficient to ablate an obstruction, it is not without its drawbacks. Most significantly, the destruction of the lesion is uncontrolled and is accompanied by thermal injury to the vessel walls immediately adjacent the obstruction. In an effort to avoid such thermal injury and to provide better control of the tissue removal, the use of a different, higher level form of laser energy having a wavelength in the ultra-violet range (40–400 nanometers) has been suggested. See, for example, International Patent Application PCT/US84/02000, published Jun. 20, 1985. One example of a laser for producing this higher level energy is known as the Excimer laser, which employs a laser medium such as argon-chloride having a wavelength of 193 nanometers, krypton-chloride (222 nm), krypton-fluoride (248 nm), xenon-chloride (308 nm) or xenon-fluorine (351 nm). The light produced by this type of laser appears in short bursts or pulses that typically last in the range of ten to hundreds of nanoseconds and have a high peak energy level, for example as much as 200 mJ. Although the destruction mechanism involving this form of energy is not completely understood, it has been observed that each single pulse of the Excimer laser produces an incision which destroys the target tissue without accompanying thermal injury to the surrounding area. This result has been theorized to be due to either or both of two phenomena. The delivery of the short duration, high energy pulses may vaporize the material so rapidly that heat transfer to the non-irradiated adjacent tissue is minimal. Alternatively, or in addition, ultraviolet photons absorbed in the organic material might disrupt molecular bonds to remove tissue by photochemical rather than thermal mechanisms.

While the high peak energy provided by Excimer and other pulsed lasers has been shown to provide improved results with regard to the ablation of atherosclerotic plaque, this characteristic of the energy also presents a serious practical problem. Typically, to couple a large-diameter laser beam into a smaller diameter fiber., the fiber input end is ground and polished to an optical grade flat surface. Residual impurities from the polishing compound and small scratches on the surface absorb the laser energy. These small imperfections result in localized expansion at the surface of the fiber when the laser energy is absorbed. The high-energy Excimer laser pulses contribute to high shear stresses which destroy the integrity of the fiber surface. Continued application of the laser energy causes a deep crater to be formed inside the fiber. Thus, it is not possible to deliver a laser pulse having sufficient energy to ablate tissue in vivo using a conventional system designed for continuous wave laser energy.

This problem associated with the delivery of high energy laser pulses is particularly exacerbated in the field of coronary angioplasty because of the small diameter optical fibers that must be used. For example, a coronary artery typically has an internal diameter of two millimeters or less. Accordingly, the total external diameter of the angioplasty system must be below two millimeters. If this system is composed of three separate optical fibers arranged adjacent one another, it will be appreciated that each individual fiber must be quite small in cross-sectional area.

A critical parameter with regard to the destruction of an optical fiber is the density of the energy that is presented to the end of the fiber. In order to successfully deliver the laser energy, the energy density must be maintained below the destruction threshold of the fiber. Thus, it will be appreciated that fibers having a small cross-sectional area, such as those used in angioplasty, can conduct only a limited amount of energy if the density level is maintained below the threshold value. This limited amount of energy may not be sufficient to efficiently ablate the obstructing tissue or plaque without thermal damage.

Even if the energy density is quite high, the small beam that results from the small diameter fiber may not have a sufficiently large target area that effective ablation of the lesion results. Only a small fragment of the lesion might be ablated, and thus not provide adequate relief from the blockage.

A further problem with the use of a fiberoptic waveguide to direct laser energy for purposes of ablating atherosclerotic plaque is that of perforation of the blood vessel. Such perforations can be caused by the waveguide itself contacting and perforating the vessel. Such perforations can also be caused by the laser beam, particularly if the waveguide is not aligned properly within the blood vessel. The perforation problems are related to the intrinsic stiffness of the glass fibers of the waveguide and poor control of laser energy, regardless of laser source or wavelength.

Also related to the stiffness of the glass fibers is the ability to control the position of the fibers radially within the blood vessels. The conventional systems employing fiberoptic waveguides within a blood vessel do not provide means for controlling radial movement within the blood vessel.

One known attempt at developing an angioplasty catheter is disclosed in U.S. Pat. No. 4,747,405. The known catheter includes a center guidewire lumen, a guidewire therein, and a single optical fiber disposed at a side of the catheter for emitting laser energy. The catheter also has a blunt leading end that does not facilitate progress through a blood vessel. A particular problem that potentially results from the disclosed arrangement of the single optical fiber and guidewire is that large segments of the lesion may become loose in the blood stream and could possibly cause an emboli. As a result, the known catheter includes a dedicated channel to remove the loosened debris.

OBJECTS AND BRIEF STATEMENT OF THE INVENTION

Accordingly, it is a general object of the invention to provide a novel system for delivering high energy pulsed laser light using an optical waveguide.

It is a more specific object of the invention to provide such a delivery system that is particularly well suited to deliver ultraviolet laser energy in vivo for the ablation of atherosclerotic plaque. In this regard, it is a particular object of the present invention to provide a highly efficient waveguide for use in such a delivery system.

It is yet another object of the present invention to provide such a delivery system that is adapted to minimize the likelihood of perforating or otherwise damaging a blood vessel in which the system is being used.

It is a further object of the present invention to provide such a system that includes a guide for facilitating the maneuvering of the optical waveguides through the blood vessel in which the system is being used.

It is another object of the present invention to provide a device for controlling the radial movement of the optical waveguide within the blood vessel in which the system is being used.

Another object of the present invention is to provide an angioplasty catheter that is able to remove lesions in small pieces so as to minimize the risk of emboli.

Briefly, one aspect of a delivery system embodying the present invention relates to a guidance system that facilitates guiding an optical filter system through a blood vessel. In a preferred form, the guidance system comprises a guidewire that is inserted into the blood vessel prior to the insertion of the optical fiber, and a sleeve having a rounded distal end and two lumens extending therethrough. The distal end of the optical fiber is bonded within one of the sleeve lumens. The wire, which has already been inserted into the blood vessel, is then threaded through the second sleeve lumen. The sleeve and optical fiber are then advanced along the wire until the optical fiber is positioned adjacent a lesion to be ablated by a laser system incorporated with the optical fiber system.

Another method is to preload the guidewire inside the guidewire lumen of the sleeve and advance the flexible leading edge of the guidewire inside the blood vessel.

Radial control of the optical fiber within the blood vessel may be obtained by locating the fiber lumen eccentrically within the sleeve. Thus by rotating the optical fiber, the optical fiber will be moved to different radial positions within the blood vessel.

In another preferred embodiment of the present invention, a multilumen, multifiber catheter is employed to deliver the laser energy to the desired site within the blood vessel. The catheter includes a central, axially disposed lumen which accommodates the guidewire. Multiple lumens located radially outwardly and circumferentially around this central lumen, or a single lumen adjacent the central lumen, house multiple fibers which are used to deliver the laser energy. With this arrangement, an output beam having a relatively large effective diameter is produced, to ablate a significant portion of the obstruction.

Further along these lines, the distal ends of the fibers can be provided with a larger diameter to cause the laser beam to expand as it exits the catheter, and thereby produce a larger area of coverage. In a preferred embodiment, the expanded beam is provided by a short length of a larger diameter fiber that is fused to the distal end of each fiber in the delivery system.

In other alternative embodiments of the present invention, balloons are retained at the distal end of the catheter so as to direct the optical fibers within the catheter.

Further features of the present invention and preferred modes for implementing them will become apparent from the following detailed description of preferred embodiments of the invention illustrated in the accompanying drawings.

BRIEF DESCRIPTION OF THE DRAWINGS

FIG. 1 is a cross-sectional side view of a delivery system for high energy Excimer laser light utilizing a funnel-shaped energy coupler;

FIG. 2 is a cross-sectional side view of a second embodiment of an energy coupler;

FIG. 5 is a perspective view of an alternative embodiment of a multilumen, multifiber catheter;

FIG. 6 is a cross-sectional end view of the distal portion of the catheter of FIG. 5;

FIG. 7 is an enlarged cross-sectional side view of the catheter of FIG. 5

FIG. 8 is a perspective view of an energy coupler according to the present invention;

FIG. 9 is a perspective view of an alternative embodiment of a large-area ablation catheter which employs multiple fibers;

FIG. 10 is an end view of an alternative embodiment of a catheter which employs balloons for displacing a fiber optic waveguide in a blood vessel;

FIG. 11 is a perspective view of an alternative embodiment of a multilumen catheter;

FIG. 12 is a perspective view of another alternative embodiment of a multilumen catheter;

FIG. 13 is a perspective view of an alternative embodiment;

FIG. 14 is a perspective view of another alternative embodiment of a multilumen catheter.

DESCRIPTION OF THE ILLUSTRATED EMBODIMENTS

Figure 3A:
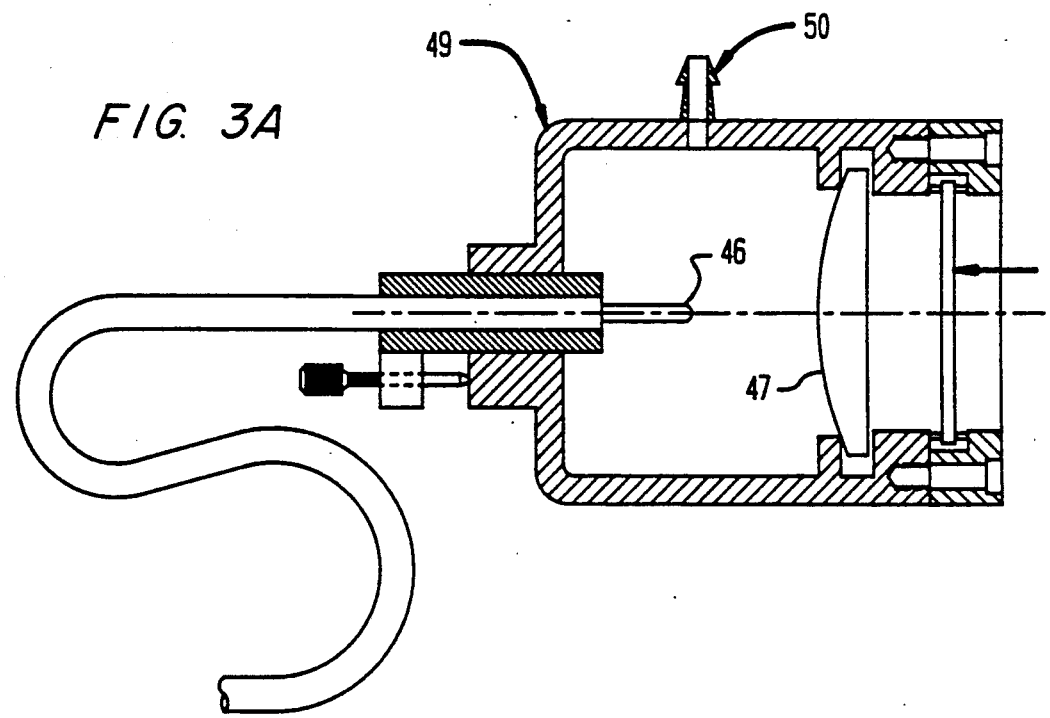
FIG. 3A is a side view, partly in section, of a third embodiment of an energy coupler.

In the following specification, a laser delivery system is described with particular reference to the use of a high energy pulsed laser, such as an Excimer laser, in an angioplasty system, to facilitate an understanding of the invention and its uses.

Referring now to FIG. 1, one embodiment of the delivery system for high energy pulsed laser light is illustrated in greater detail. The delivery system comprises two basic elements. One of these is the optical fiber 12, and the other is the energy coupler 30. A fiber that is particularly suitable for use in the delivery of high energy pulsed ultraviolet laser light is a multi-mode fiber which has a relatively large core, or active area, relative to the area of its cladding, i.e., the outer skin of the fiber. The core is made of substantially pure synthetic fused silica, i.e., amorphous silicon dioxide. This material preferably has a metallic impurity content of no more than 30 parts per million, to provide better conduction of the transmitted laser energy than that which is obtainable with natural fused quartz. The term "metallic impurity" includes both metals per se and oxides thereof.

Even with such a low level of metallic impurity, defects in the silica fiber can serve as linear and non-linear absorption sites for the photons. These defects can vary from oxygen vacancy to unbonded silicon atoms found in any silica glass. They can result in lowered transmittance of ultraviolet radiation. Increasing the intensity (or energy) of the laser light that is introduced into one end of a fiber exhibiting such defects will not necessarily result in proportionally increased output at the other end. Rather, the increased intensity level can reduce the threshold level at which bulk damage occurs to the silica glass, and thereby destroys the delivery system.

In accordance with one aspect of the present invention, the transmittance of high energy UV laser light in a fiber made of synthetic silica is enhanced by lightly doping the silica with a material which functions to repair some of the inherent structural defects of the silica. The silica is preferably doped with an $OH^-$ radical, to thereby form so-called "wet" silica. It is believed that defects in silica that affect UV light transmission comprise oxygen hole centers and unbonded silica atoms. It is theorized that the doping of the silica with the $OH^-$ radical functions to repair these defects by eliminating the oxygen holes or vacancies in one case and by bonding to the silicon to form the $SiO_2$ double bond. It has been reported that pure silica having only about 5 parts per million (ppM) of an OH radical has an absorption coefficient which is 2–3 times greater than silica having about 1200 ppM of the radical. See J. H. Stathes et al, *Physical Review B.*, Vol. 29, 12, 1984, pp. 70–79. Other investigations have reported that an optical absorption band appears in silica fibers having a low $OH^-$ content as a result of the fiber drawing process. See Kaiser et al, *J. Opt. Soc. Am.* 63, 1973, p. 1141 and *J. Opt. Soc. Am.* 63, 1974, p. 1765. Apparently, an increase in the $OH^-$ content of silica reduces both types of absorption sites described above, and in accordance with the present invention this concept is applied to a system for delivering high peak energy ultraviolet laser pulses to thereby enhance the efficiency of the energy transmittance. Preferably, the silica that makes up the fibers contains about 200 to 2000 ppM of the $OH^-$ radical, most preferably 1200 ppM.

In another embodiment of the invention, the silica that is used to produce the fibers of the delivery system is doped with fluorine. Fluorine doped silica exhibits even lower attenuation than high OH silica. It appears that the fluorine functions to shift the absorption band gap in the $SiO_2$ structure, to facilitate the transmittance of a large number of photons at low wavelengths. For multimode fibers having diameters in the range of 100 micrometers to 1500 micrometers, the silica preferably should contain between 0.25 and 2.0 wt % fluorine, most preferably 1.0 wt %.

As a further feature of the invention, the silica can be doped with both the $OH^-$ radical and fluorine. When both of these materials are used in combination, the OH radical content should range between 200 and 2000 ppM, and the fluorine should comprise between 0.5 and 3 wt % of the silica.

In the context of the present invention, the fiber can be a single fiber or a bundle of fibers having a total diameter in the range of 100–2,000 microns. A bundle of close-packed small-diameter fibers is preferred because they provide greater overall flexibility and thereby more easily accommodate the twists and tight turns that are required to feed the delivery system through body cavities. This is particularly desirable where a larger diameter waveguide is required to deliver a relatively large diameter beam with uniform intensity, such as in vascular angioplasty. This entire structure can be surrounded by a protective flexible jacket 28 made of a material which is not damaged by ultraviolet light. More particularly, when the fiber undergoes sharp bends, for example at the juncture of two arteries, light losses occur. These losses may be enough to melt some types of jacket materials such as silicone and nylon. However, UV light resistant materials, for example UV cured acrylate compound or TEFLON ®, can sustain high bending losses without degradation and are therefore more desirable for the jacket.

In a preferred form of the invention, the protective jacket is incorporated as part of the fiber itself, rather than being a separate piece of structure which surrounds all of the fibers. As noted previously, every fiber comprises a core and a cladding which surrounds the core to maintain the transmitted light energy within the core. The cross-sectional area of the fiber might normally have a core/cladding ratio of 80/20 to provide suitable flexibility. Typically, both the core and the cladding are made of glass, with the cladding being appropriately modified (e.g., doped) to provide it with a lower index of refraction. In this conventional structure, the protective jacket comprises a third layer which surrounds the core and cladding.

In accordance with one aspect of the invention, the conventional glass cladding is eliminated and the core of the fiber is directly surrounded by a coating of organic material. One specific preferred material is UV-cured acrylate. It has a lower index of refraction than silica, and thereby functions to maintain the laser energy within the core. It also serves to protect the silica glass, and hence eliminates the need for a third layer. This reduces the overall size of the fiber and hence enables the net cross-sectional area of the core to be increased for a delivery system having a given outer diameter.

Further details regarding the composition of preferred coatings can be found in U.S. Pat. No. 4,511,209, the disclosure of which is incorporated herein by reference.

A silica fiber of this construction can typically accommodate input energy up to a level around 30 mJ/mm$^2$ produced by a commercially available Excimer laser with a 10–40 pulse. If the density of the energy is increased above this level, the input end of a conventional fiber having a planar, polished surface will be damaged or destroyed if the laser is applied directly to it. Unfortunately, this density level is about the minimum that is required to produce ablation of calcified plaque, thus providing no tolerance range if the intended use of the delivery system is for angioplasty. Accordingly, to enable a higher level of energy to be conducted in the fiber, an energy coupler 38 can be provided at the input end of the fiber. In the embodiment illustrated in FIG. 2, this energy coupler comprises a section of fiber that has a larger cross-sectional area than the main portion of the fiber. This larger cross-sectional area gradually tapers to the nominal diameter of the fiber, to provide a funnel-shaped input section.

Production of such a shape on the end of the fiber can be accomplished by appropriate design of the die through which the silica is drawn to produce the fiber. By interrupting the drawing of the fiber, a bulbous mass remains at one end of the fiber. This mass can be cut and polished to produce the funnel-shaped input section.

In operation, the increased area of the funnel-shaped coupler decreases the input energy density for a given level of energy within the fiber. Accordingly, the area of the input end can be appropriately dimensioned to enable a sufficient amount of energy for ablation of tissue to be coupled into the fiber without damaging the input end. Once it has been coupled in, the density of the energy is increased by decreasing the cross-sectional area of the fiber within the tapered section, so that a greater amount of energy can be conducted within the fiber than would be possible without such a device.

A second embodiment of an energy coupler is illustrated in FIG. 2. In this embodiment, the optical fiber has a uniform diameter along its length and terminates at a flat polished end. The end section of the fiber is encased within a ferrule 32 made of a suitable material such as brass, for example. An aluminum casing 33 having an annular ring 34 projecting from the inner wall thereof is threaded onto the ferrule. A TEFLON ®O-ring 35 disposed between the end of the annular ring and the ferrule provides a watertight seal between the casing and the ferrule. A second O-ring 36 is disposed on top of the annular ring and supports a glass plate 38 made of z-cut quartz, for example. This arrangement forms a fluid-tight cavity 40 between the ferrule 32, the casing 33 and the glass plate 38. The glass plate can be held in place by means of a third O-ring 42 and a clamping ring 44 disposed on the top of the casing. The fluid tight cavity is filled with liquid which acts as a buffer to the input end of the fiber, enabling laser energy having a relatively high density to be coupled into the fiber without damage thereto. The liquid within the cavity can be distilled and deionized water, or it can be a transparent oil having an index of refraction that is matched to that of the fiber 12, for example.

Figure 3B:
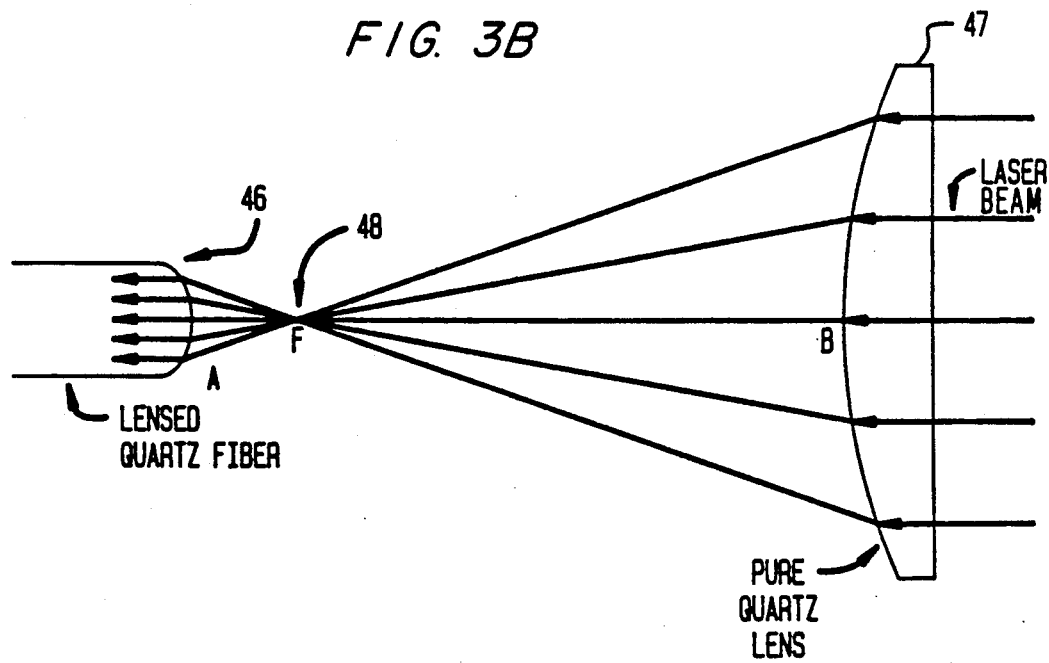
FIG. 3B is an enlarged view of a portion of FIG. 3A, illustrating the principle of operation of this embodiment.

A third, and preferred, embodiment of an energy coupler is illustrated in FIGS. 3A and 3B. In this embodiment, the input end of the fiber is provided with a fused semispherical lens 46. This lens can be formed by melting the material of the fiber itself with a microtorch, to produce a high purity silica lens with no impurities or cracks. Alternatively, the lens 46 can be a separately ground lens that is attached to the flat end of the fiber. The fiber 12 can be tapered as shown in FIG. 2, or it can have a uniform diameter along its length.

A second lens, preferably a plano-convex lens 47, focuses the input beam from the laser to a focal point 48. The input lens 46 on the fiber is axially aligned with the lens 47 and is located at a distance from the lens 47 which is greater than the focal length of that lens. Thus, the focused laser energy appears to be coming from a point source. The lens 46 collimates this focused energy and couples it into the fiber.

The input end of the fiber with the lens 46 and the focusing lens 47 are housed within a chamber 49. This chamber is provided with a vacuum port 50 to enable the chamber to be evacuated of air. If air were present between the lenses 46 and 47, the highly concentrated energy at the focal point 48 might cause a breakdown of nitrogen and oxygen gases that could contaminate the lens 46. In addition, the vacuum environment keeps out dust and other particles which could settle on the lens 46 and act as a heat sink, destroying the roundness of the lens.

Alternatively, this chamber 49 can be filled with a liquid, such as water or oil for example, which matches the index of refraction of the silica fiber. The higher index of refraction of the liquid reduces the dielectric shock when the pulse propagates from the liquid transmission medium to the fiber, relative to that which is experienced when air is the transmission medium.

Although the preferred embodiment employs a curved lens at the proximal input end of the fiber, it is possible to couple the energy into a fiber having a planar input surface. However, it is important to ensure that this surface is free of scratches and other imperfections. This can be accomplished by heating the end of the fiber with a micro-torch to cause the fiber material to melt and flow slightly, thereby removing the imperfections caused by polishing.

The type of energy coupler shown in FIG. 3A serves to amplify the energy within the fiber. More particularly, the amplification factor is equal to the ratio of the diameter of the laser beam at the lens 47 to the diameter of the fiber. This ratio is also related to the magnification produced by the two lenses. Referring to FIG. 3B, the dimension FB is the focal length of the lens 47 and the dimension FA is the distance between the lens 47 and the focal point 48. The magnification factor of these two lenses is defined as FB/FA. Since this factor must be equal to the laser energy amplification, the appropriate distance between the lenses 46 and 47, i.e., AB=FB+FA, can be determined from the following relationship:

$$\frac{FB}{FA} = \frac{D_L}{D_F}$$

where $D_L$ is the diameter of the laser beam and DF is the diameter of the fiber.

Although illustrated as a separate element in the figures, it will be appreciated that the energy couplers could be incorporated into the structure of a laser, to provide an integrated laser and coupling system.

Thus, with the combination of the lightly doped synthetic silica fiber and the energy coupler 30 that enables a greater level of energy to be conducted through the fiber, an amount of high energy laser light that is sufficient to produce an incision can be safely transmitted through an optical fiber waveguide without the risk of damage to the fiber.

To further increase the peak energy that is delivered through the system, it is preferable to slightly increase the length of the pulses beyond the relatively short duration that is typically produced by commercial Excimer lasers and the like. For example, a pulse having a duration in the range of 10-3000 nsec, more preferably 100-300 nsec, enables much higher peak energy to be applied with the same delivery system than a 10 nsec pulse yet is still sufficiently short to produce the desired cutting action. One example of a circuit for stretching the output pulses of a laser is the magnetic switch developed at the Jet Propulsion Laboratory by Drs. J. Ladunslager and T. Tacala. In this regard, it is not necessary that each lengthened or stretched pulse comprise a single, continuous pulse having a duration of 100-300 nsec, for example. Rather, it could comprise a burst of shorter length successive pulses which together provide an effective pulse length of the desired duration.

With the increased energy that is provided by the lengthened pulses, the energy level within the fiber will likely be more than sufficient to enable the laser beam to ablate an obstruction. In fact, the beam could be expanded as it exits the fiber and still contain sufficient energy density to ablate tissue. By expanding the diameter of the laser beam, for example by means of an increasing taper or fusing a larger diameter fiber at the distal end of the fiber, a larger area of tissue is ablated to produce more favorable results towards obtaining better blood flow in a blood vessel while using a small diameter flexible fiber that can be easily propagated through the vessel.

In an additional method of coupling a substantially pure silica fiber delivery system to the high energy pulsed laser, an energy coupler may be used. With reference to FIG. 8, a pure silica fiber 102 is tapered at about a one degree (1°) taper and is about 30 centimeters long. The fiber 102 has an input end 104 with a diameter of about 15 mm. At the narrow end 106 of the fiber 102 is a modular connector 106 that connects with a connector 108 on the end of the optical waveguide A source 112 of laser energy propagates laser energy into the tapered fiber 102 such that, in a preferred embodiment the energy density at the connector 106 is about 50-100 milliJoules/mm$^2$.

Figure 4:
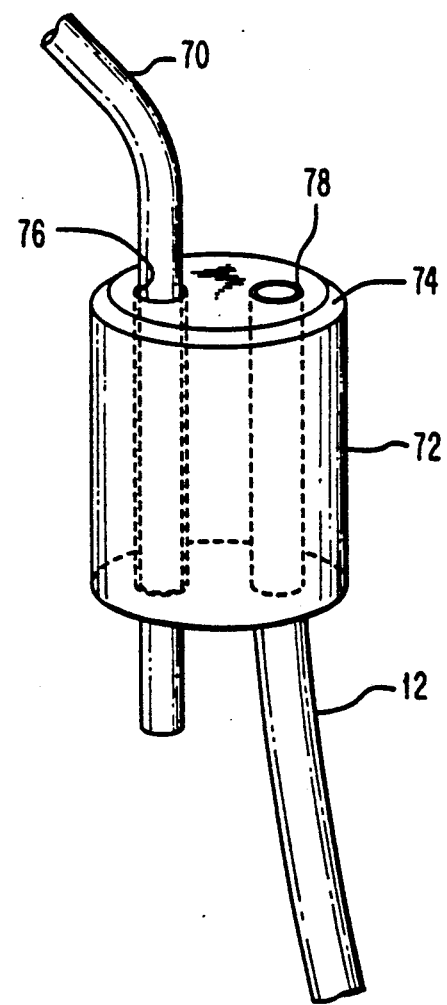
FIG. 4 is a perspective view of a guidewire and sleeve used to control movement of the waveguide.

In order to provide better control of the optical fiber 12, a guidance system may be employed. Referring now to FIG. 4, the guidance system includes a guidewire 70 and a sleeve 72.

The sleeve 72 is preferably between 1 and 200 centimeters in length, and has a rounded tip 74 at its distal end. The tip 74 can be made of stainless steel and glued or welded to the sleeve, or it can be formed integrally on the sleeve 72. The diameter of the tip can vary from 1.2 to 2.5 mm, depending upon the size of the blood vessel. The rounded tip 74 serves as both a dilator to enlarge the blood vessel and as a device to blunt the tip of the optical fiber 12 so as to minimize trauma to the blood vessel.

The sleeve 72 has at least two lumens 76, 78 therein. A first lumen 76 is designed to accept the guidewire 70 and is preferably within the range of twelve-thousandths (0.012) to thirty-eight thousandths (0.038) of an inch in diameter. The diameter of the first lumen may vary, depending on the diameter of the guidewire 70.

The second sleeve lumen 78 is designed to enclose the optical fiber 12, or an array of fibers, if such is the case. The diameter of the second lumen 78 may also vary according to the diameter of the optical fiber 12 or fibers being used. The distal end of the optical fiber 12 is bonded within the second lumen 78 by any suitable means well known to those skilled in the art of bonding.

To use the guidance system, the guidewire 70 is threaded through the lumen of the blood vessel by means of an introducer catheter (not shown). The guidewire 70 is inserted up to the location of a total obstruction in the vessel, or in the case of a subtotal lesion, beyond the lesion.

The sleeve 72 is then mounted onto the guidewire 70, with the guidewire extending through the first lumen 76 of the sleeve. The sleeve 72 and the optical fiber 12, which is bound thereto, are then advanced along the guidewire 70 until the sleeve 72 and the distal tip of the optical fiber 12 are adjacent the lesion to be ablated. The combination of the guidewire 70 and the sleeve 72 ensures that the optical fiber 12 remains in alignment with the blood vessel, thus avoiding perforation of the blood vessel by the tip of the optical fiber 12 during positioning of the fiber or by the laser beam during ablation.

Alternatively, the guidewire 70 may initially be threaded through the first lumen 76 of the sleeve 72, prior to the insertion of the guidewire 70 into the blood vessel.

Once the fiber 12 is adjacent the lesion, ablation of the lesion is conducted as described above. In a preferred embodiment, the second lumen 78 is eccentrically located within the sleeve 72. In such an arrangement, rotation of the optical fiber 12 while it is in the blood vessel causes rotation of the sleeve 72 which causes the radial position of the optical fiber 12 to shift within the blood vessel. Accordingly, rotating the optical fiber 12 during lasing causes a larger lumen to be ablated within the blood vessel.

Once the lasing is completed, the sleeve 72 and the optical fiber 12 can be withdrawn, leaving the guidewire 70 in place within the blood vessel. Angiographic dye can then be injected through a guiding catheter around the guidewire 70 to evaluate the results of the lasing operation. If the results are unsatisfactory, the entire procedure can be repeated, possibly using different laser parameters or fibers.

A further, preferred embodiment of a catheter for coronary laser angioplasty, which operates in accordance with the foregoing principles, is illustrated in FIGS. 5-7. The catheter 80 is multi-compartmented. It includes a center lumen 82 which accommodates a guide wire 84. The guide wire is introduced through a suitable coupling device 86 at the proximal end of the catheter. The center lumen 82 is surrounded by a plurality of circumferentially disposed outer lumens 88. These lumens 88 each house one or more substantially pure synthetic silica fibers 90. In the illustrated embodiment there are three outer lumens 88 each housing two fibers 90. It will be appreciated that a different number of lumens and/or fibers per lumen can be employed, as determined by the relative sizes of the fibers 90, the guide wire 84 and the diameter of the catheter. Furthermore, the guide wire lumen may be eccentrically arranged within the catheter.

An enlarged cross-sectional side view of the distal end of the catheter is shown in FIG. 7. Here, each laser-energy conducting fiber 90 is fused at its end face 91 to a short section of a larger diameter fiber 92. For example, the fibers 90 might have a diameter of 200 microns throughout the length of the catheter 80, and the short end fibers 92 might have a diameter of 300 microns, or a 100 micron diameter fiber may have a short 200 micron diameter fiber fused to its end. Each end fiber 92 can be about 3 mm long, and can be made from the same silica material as the fibers 90. By virtue of the larger diameter fiber at the distal end, the laser beam can expand as it emerges from the fiber, thereby providing a larger area of coverage and subsequently a larger ablation area. Furthermore, the plural fibers located symmetrically around the guidewire provide uniform energy distribution over a larger area.

The fibers 92 are held in place at the end of the catheter by means of a suitable epoxy 94. A gold marker ring 96 can be provided around the catheter at the distal end, to assist in locating the end of the fiber during a fluoroscopy and angiography procedure.

Except at the very end of the catheter where the epoxy 94 is present, there is free space within each outer lumen 88 between the fiber 90 and the walls of the lumen. If desired, this free space can be used to provide a saline solution, or other contrast media, to the site of the obstruction. The solution can be injected into the catheter through a suitable port 98 at the proximal end, and emerge through holes 100 in the side wall of the catheter at its distal end (see FIG. 7).

In certain situations, there is a need to ablate a large area of a partially or fully occluded vessel in order to maintain an open lumen. The clinical efficacy of ablation in the large peripheral vessels is enhanced when the lumen created is larger than 2 mm. Long term reocclusion of large vessels with low pressure blood flow is reduced when the energy delivery system is used to ablate a hole without subsequent dilation of the vessel.

The following new systems address the problems of making large diameter holes in blood vessels using a small overall diameter delivery system. Turning attention now to FIG. 9, a blood vessel 114 is shown with a lesion 116 therein. A catheter 118 includes a plurality of optical fibers 120 evenly distributed about a concentrically mounted inflatable balloon 122. The optical fibers 120 may be 100–400 microns. A guidewire 124, larger than 0.012 inches in diameter, is concentrically located in a center lumen within the balloon 122. If desired, a metallic (gold) marker 126 may be located adjacent the distal end of the catheter, such that the catheter 118 may be located by an x-ray or fluoroscopy system.

In operation, the guidewire 124 is inserted through the lumen or blood vessel 114 until the guidewire passes through the lesion 116 that is to be ablated. The catheter 118 is then conveyed along the guidewire 124 until the distal end of the catheter 118 contacts the lesion 116. The fibers 120 deliver an initial dose of high energy laser pulses to ablate the inner portion of the lesion 116. Subsequently, the balloon 122 is inflated to a predetermined pressure which then forces the fibers 120 into an array of a larger diameter. A subsequent delivery of high energy pulsed laser is then delivered to ablate the outer peripheral portions of the lesion 116. The balloon 122 may be additionally inflated if necessary to obtain an array of fibers 120 of a still larger diameter.

With reference to FIG. 10, an additional preferred embodiment of the present invention is disclosed. A catheter 128 has three balloons 130 located in an equally spaced arrangement at the distal end of the catheter 128. A first lumen 132 is positioned concentrically among the balloons 130. In the first lumen 132 is disposed a fiber optic instrument 133. If desired, a guidewire may be retained in a second lumen adjacent the first lumen 132. Additional lumens may also be included at the center of the balloons 130 to accommodate other instruments to assist with illumination or flushing, for example.

In operation, the lumens at the center of the catheter may be positioned or tilted by selectively inflating and deflating the three balloons 130. In one mode of operation, the balloons may be inflated sequentially and continuously so as to selectively revolve the fibers in a circular pattern along the perimeter of the catheter. The fibers may be centered by inflating all of the balloons.

In another embodiment, two, four or any other number of balloons may be used instead of three.

As in the embodiment shown in FIG. 9, the embodiment shown in FIG. 10 may, also include a marker, such as a gold band, at the distal end of the catheter.

Another preferred embodiment of the present invention is illustrated in FIG. 11. In this embodiment a guidewire 150 has a balloon 152 at the end thereof. Markers 154 are mounted on the guidewire 150 adjacent the balloon 152. The guidewire 150 is disposed through a guidewire lumen 164 in the center of a catheter 160. The catheter 160 further includes a plurality of fibers 162 arranged in an annular pattern about the guidewire lumen 164. If desired, a marker 166, such as a gold band, can be placed around the distal end of the catheter 160 to facilitate detection of the catheter.

In operation, the guidewire 150 with the balloon 152 at one end thereof is inserted through the blood vessel until it is located beyond the lesion 158. The balloon 152 is then inflated, thus centering the guidewire 150 within the vessel. Such centering of the guidewire 150 minimizes the likelihood that the catheter 160 will contact the walls of the blood vessel 156 during the ablation process. A stop 168 may be placed on the guidewire 150 so as to prevent the catheter 160 from contacting and thus possibly rupturing the balloon 152.

The fibers 162 in the catheter preferably range from about 50 to 300 microns. The guidewire lumen 164 is large enough to allow free movement over a standard guidewire ranging from 0.014 to 0.038 inches in diameter.

With reference to FIG. 12, another preferred embodiment of the present invention is disclosed within a blood vessel 170 having a lesion 172 therein. A catheter 174 includes a guidewire and flushing lumen 178 located adjacent an inner edge of the catheter. An optical fiber lumen 176 has a width that extends from the guidewire and flushing lumen 178, through the center of the catheter to the edge of the catheter diametrically opposite the guidewire and flushing lumen 178. A plurality of optical fibers 180 made of substantially pure silica are disposed within the optical fiber lumen 176, and a guidewire 182 is disposed within the guidewire and flushing lumen 178. A balloon 184 is bonded at one point to the outer surface of the catheter 174.

To operate, an initial ablation is performed with the balloon 184 in an uninflated condition. The ablation is effected by delivering a high energy pulsed laser, such as from an Excimer laser, through the optical fibers 180 while advancing and rotating the fibers about the guidewire 182. The rotation enables the fibers to ablate a circular area about the size of the catheter outer diameter.

In the next stage, the outer balloon is inflated, thus urging the fibers into a larger diameter. A second ablation is performed with the balloon inflated and while advancing and rotating the catheter so as to ablate an annular area having a diameter larger than the diameter of the circular area ablated during the first stage. During the second stage, the balloon is inflated to a predetermined size in order to ensure that the second annular area is contiguous to the circle ablated during the first stage.

The Excimer energy is only capable of ablating a lesion in a forward direction and does not require that the blood between the lesion and the optical fibers be displaced with a solution, such as saline, that is transparent to the laser. In addition, the laser transmitted through the optical fibers is capable of ablating a lesion in a blood field. Therefore, there is no necessity to block the blood flow around the catheter during the ablation process.

The tip of the catheter should have a round, conical, distal tip to minimize the trauma to the vessel wall. The optical fibers 180 comprise a highly flexible array of fibers that may range in size from 100 to 400 microns in diameter, with a possible enlarged fiber tip output diameter to create a large ablation area. The fibers which are immobilized at the distal end of the catheter by epoxy are polished to form the round distal tip.

The guidewire used to advance the catheter over is commonly used in interventional radiology and cardiology and is preferably larger than 0.012 inch.

If desired, markers 186, such as gold bands can be placed at the distal of the catheter to facilitate monitoring of the catheter by x-ray or fluoroscopy.

With reference to FIG. 13, a catheter 174' is disclosed that is substantially the same as the catheter 174 of FIG. 12, described above. The significant difference between the catheter 174 of FIG. 12 and the catheter 174' of FIG. 13 is that the balloon 184' of FIG. 13 includes a recess 188' that enables blood to flow around the balloon 184' during its use.

The off-center balloon catheters of the present invention function differently from other balloon catheters that are used in interventional cardiology and radiology. The off-center balloon catheters of the present invention are not dilation devices, such as those used in Percutaneous Transluminal Angioplasty (PTA) and Percutaneous Transluminal Coronary Angioplasty (PTCA). They are not intended to laterally dilate the blood vessels in which they are used or to press a catheter against the wall of a vessel. They also are not intended to stop the flow of blood and replace it with saline, as is commonly done to improve visualization during angioscopy. Rather, they function as positioning devices which enable the optical fibers, and hence the high energy laser, to be precisely positioned within the blood vessel. In this regard, they are not intended to contact the walls of the blood vessel tightly, so that translation and/or rotation of the catheter is possible while the balloons are inflated, to thereby provide a mobile angioplasty operation.

With reference to FIG. 14, another embodiment of the present invention is illustrated within a blood vessel 190 having a lesion 192 therein. A catheter 194 has a smooth, rounded leading edge 196, which may be lubricous, e.g., coated with a water repellant chemical, for easy advancing and/or rotation through a blood vessel.

In the center of the catheter 194 is a guidewire lumen 198, within which lumen a guidewire 200 is slidably disposed. Surrounding the central guidewire lumen 198 is an annular array of optical fibers 202 that may be used to deliver high energy pulsed laser for ablating the lesion 192. A balloon 204 is mounted to a location on the outer periphery of the catheter 194.

In operation, the guidewire 200 is first threaded through the blood vessel 190 until it is adjacent the lesion 192. The catheter 194 is then conveyed along the guidewire 200 with the balloon 204 deflated until the catheter 194 is adjacent the lesion 192. At that point, a channel is ablated in the lesion 192 with laser energy delivered by the optical fibers 202. The size of the channel is substantially equal to the outside diameter of the catheter 194. The balloon 204 is then inflated, thus shifting the optical fibers 202 to a higher orbit. The lesion 192 is again ablated by the optical fibers 202 while advancing and/or rotating the catheter, thus forming a larger opening within the lesion 192. The balloon 204 may be further inflated, and the process repeated, as necessary.

As a result of the embodiment disclosed in FIG. 14, the lesion 192 is uniformly ablated by a plurality of optical fibers 202. As a result, the likelihood of large segments of the lesion 192 being released into the blood flow, where they may cause emboli down stream is substantially reduced. Because the lesion 192 is broken into small segments, there is no need to have a dedicated channel in the catheter to remove debris. The system disclosed in FIG. 14 generally creates particles less than 10 $\mu$ in diameter.

Figure 15:
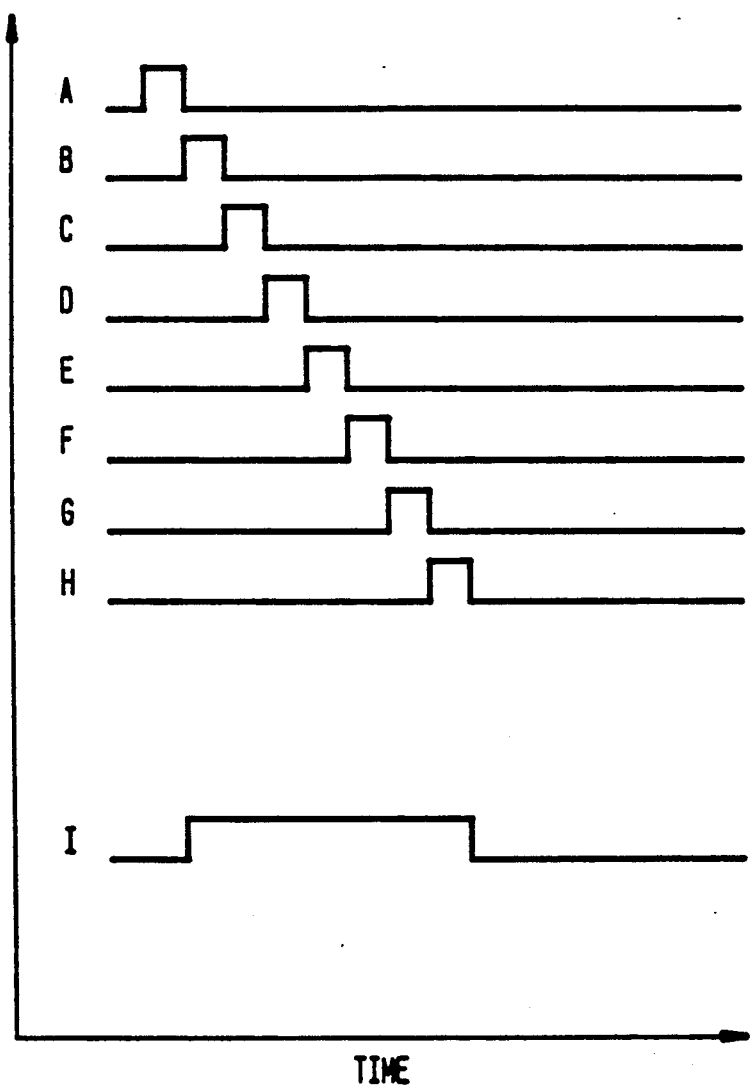
FIG. 15 is a graph showing pulse construction.

FIG. 15 relates to a method of transmitting high energy pulsed laser beams through a substantially pure silica fiber. FIG. 15 depicts a pulse that is made up of a train or a group of time shifted subpulses. A high energy long pulse I is a super positioning of numerous (subpulses) A-H and has a shorter diffusivity of tissue. In other words, a high energy pulse duration can be stretched in time when ablating a tissue without causing undesired thermal damage to adjacent tissue due to the thermal diffusion through the tissue during the ablation process. The estimated time needed to move a high energy laser pulse from an ablation zone tissue is about one millisecond.

U.S. Pat. No. 4,677,636 relates to such laser pulses, and the subject matter thereof is incorporated herein by reference.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. An angioplasty system for providing radiant energy to a remote site at an energy level that is sufficient to ablate biological tissue, comprising:
   a source of pulsed ultraviolet laser energy; and optical means comprising at least one optical fiber that is silica and substantially free of metallic impurities disposed within a jacket made from a material that is not degraded by ultraviolet light substantially more than polytetrafluoroethylene would be degraded, for conducting laser energy from said source to said remote site;

wherein each pulse of energy has an energy density of at least 50 mJ/mm$^2$ at a proximal end of said optical means.

2. The angioplasty system of claim 1, wherein said material is a UV-cured epoxy.

3. The angioplasty system of claim 1, wherein said material is polytetrafluoroethylene.

4. An angioplasty system for providing laser energy to a remote site at a level that is sufficient to ablate biological tissue, comprising:

a source of pulsed ultraviolet laser energy, wherein each pulse of energy from said source has a duration substantially greater than 10 nsec; and fiber-optic means that are silica and substantially free of metallic impurities for conducting the laser energy from said source to said remote site;

wherein each pulse of energy has an energy density of at least 50 mJ/mm$^2$ at a proximal end of said fiber-optic means.

5. The angioplasty system of claim 4, wherein said fiber optic means comprises a multiplicity of said optical fibers.

6. The angioplasty system of claim 4, wherein said pulses each have a duration in the range of 100–3000 nsec.

7. The angioplasty system of claim 4, wherein the duration is at least 100 nsec.

8. The system of claim 4, wherein each pulse of energy has a duration less than or equal to 3000 nsec.

9. The angioplasty system of claim 4, wherein said synthetic silica is doped with an OH$^-$ radical.

10. The angioplasty system of claim 9, wherein said synthetic silica contains about 200 to about 2000 ppM of said OH$^-$ radical.

11. An angioplasty system, comprising:

a source of pulsed ultraviolet laser energy, wherein each pulse has a duration of at lest 100 nsec;

fiber optic means for receiving said laser energy from the source at a proximal end of the fiber optic means and delivering said energy to a predetermined site forwardly of a distal tip thereof, said fiber optic means having a first diameter throughout a substantial portion of the length of the fiber optic means;

each pulse of energy has an energy density of at least 50 mJ/mm$^2$ at the proximal end of said fiber optic means; and means at said distal tip of said fiber optic means having a second diameter larger than said first diameter for expanding a diameter of a beam of laser energy emerging from said distal tip;

said fiber optic means being silica and substantially free of metallic impurities.

12. The system of claim 11, wherein said expanding means comprises a length of optical fiber fused to the distal end of said fiber optic means.

13. The system of claim 11, wherein the source is a source of pulsed laser energy, wherein each pulse of energy has a duration in the range of 100 to 3000.

14. The system of claim 13, wherein each pulse of energy is made up of a train of time-shifted pulses.

15. The system of claim 13, wherein each of said laser pulses has a duration in the range of 100–300 nsec.

16. An angioplasty system, comprising:

a source of pulsed ultraviolet laser energy, wherein each pulse of energy has a duration greater than 10 nsec;

an elongated catheter adapted to fit within a human blood vessel, said catheter being divided into at least first and second lumens;

a guidewire disposed in said first lumen and longitudinally slidably with respect to said catheter;

a plurality of silica fiber-optic means disposed in said second lumen and extending to the distal tip of said catheter for emitting laser energy forwardly of said distal tip of said catheter, said fiber-optic means being substantially free of metallic impurities;

wherein each pulse of energy has an energy density of at least 50 mJ/mm$^2$ at a proximal end of said catheter; and means for coupling the pulsed laser energy from said laser into one end of said fiber-optic means.

17. The angioplasty system of claim 16 wherein said first lumen is located at approximately a center of said catheter and a second lumen is located radially outward of said first lumen.

18. The angioplasty system of claim 16, wherein the fiber-optic means are arranged concentrically about the guidewire.

19. The system of claim 16, wherein each pulse of energy has a duration less than or equal to 3000 nsec.

20. The angioplasty system of claim 16 wherein each of said pulses has a duration of in the range of 100–3000 nsec.

21. The angioplasty system of claim 20 wherein each of said pulses comprises a sequence of time-shifted pulses.

22. The angioplasty system of claim 16, wherein a first portion of said fiber-optic means have a first diameter throughout a first portion of said catheter, and further including a second portion of said fiber optic means at a distal end of said fiber optic means for expanding a diameter of a beam of laser energy emerging from said fiber optic means to a diameter larger than said first diameter, wherein the pulses of energy are at least 100 nsec in duration.

23. The angioplasty system of claim 22 wherein said second portion comprises a plurality of lengths of optical fiber having a diameter larger than said first diameter, said lengths of fiber being respectively fused to said distal end of said waveguides.

24. An angioplasty system for providing laser energy to a remote site in a blood vessel at a level that is sufficient to ablate biological tissue, comprising:

a source of pulsed ultraviolet laser energy, wherein each pulse has a duration of at least 10 nsec; and a plurality of optical means for conducting the laser energy from said source to said remote site, comprising a multiplicity of synthetic silica fibers which provide greater flexibility than a single fiber of comparable net cross-sectional area while enabling said laser energy to be delivered to said site in a beam having an ablating area similar to that which would be delivered by the single fiber of comparable net cross-sectional area, said fibers being substantially free of metallic impurities;

wherein each pulse of energy has an energy density of at least 50 mJ/mm$^2$ at a proximal end of said silica fibers.

25. The system of claim 24, wherein each pulse of energy has a duration less than or equal to 3000 nsec.

26. The angioplasty system of claim 24, wherein each pulse has a duration of at least 100 nsec.

27. The angioplasty system of claim 26, wherein said synthetic silica is doped with an OH$^-$ radical.

28. The angioplasty system of claim 7, wherein said synthetic silica contains about 200 to about 2000 ppM of said OH$^-$ radical.

29. The angioplasty system of claim 26, wherein said optical waveguide further comprises a jacket in which said multiplicity of fibers are disposed.

30. The angioplasty system of claim 29, wherein said jacket is made from a material that is not degraded by ultraviolet light.

31. The angioplasty system of claim 30, wherein said material is a UV-cured epoxy.

32. The angioplasty system of claim 30, wherein said material is polytetrafluoroethylene.

33. A system for the delivery of pulsed laser energy during angioplasty, comprising:
   a elongated catheter having a proximal end adapted to fit within a human blood vessel, said catheter being internally divided into a plurality of lumens and having a distal tip;
   a guidewire disposed in one of said lumens, said lumen in which said guidewire is disposed being located in the center of said catheter along a longitudinal axis of the catheter;
   a second lumen located radially outwardly of said center guidewire lumen and concentric with respect thereto;
   a plurality of fiber-optic means extending within said second lumen to the distal tip of the elongated catheter in a symmetrical relationship relative to said guidewire for emitting laser energy passing therethrough forwardly of said distal tip of said catheter, said fiber-optics means being silica and substantially free of metallic impurities; and
   a pulsed laser source of ultraviolet photons, wherein each pulse has an energy density at the proximal end of the catheter of at least 50 milliJoules per square millimeter, and wherein each pulse of energy has a duration greater than 10 nsec.

34. The system of claim 33, further comprising an annular balloon radially disposed about said catheter.

35. A system for the delivery of pulsed laser energy during angioplasty, comprising:
   an elongated catheter adapted to fit within a human blood vessel, said catheter being internally divided into a plurality of lumens and having a distal tip;
   a guidewire disposed in one of said lumens, said lumen in which said guidewire is disposed being located in the center of said catheter along a longitudinal axis of the catheter;
   a second lumen located radially outwardly of said center guidewire lumen and concentric with respect thereto;
   a plurality of fiber-optic means extending within said second lumen to the distal tip of the elongated catheter in a symmetrical relationship relative to said guidewire for emitting laser energy passing through said fiber optic means forwardly of said distal tip of said catheter, said fiber-optic means being silica and substantially free of metallic impurities; and
   a pulsed laser source of ultraviolet photons, wherein each pulse has at least 50 mJ/mm$^2$ at a proximal end of said catheter and has a duration greater than 100 nsec.

36. The system of claim 35, wherein each pulse of energy has a duration time less than or equal to 300 nsec.

37. A method of angioplasty, comprising:
   mounting a silica optical fiber that is substantially free of metallic impurities in a first longitudinal passage in a sleeve having a leading edge such that the distal end of the optical fiber is flush with the leading edge of the sleeve;
   threading a guidewire through a second longitudinal passage in said sleeve, said second passage being parallel to the first passage;
   inserting the guidewire into a lumen;
   conveying the sleeve and optical fiber along the guidewire until the optical fiber is adjacent an intravascular lesion; and
   ablating said lesion with pulsed ultraviolet laser energy, wherein each pulse has at least 50 mJ/mm$^2$ at a proximal end of said fiber.

38. The method of claim 37, wherein the threading step includes inserting the same end of the guidewire that is threaded through the sleeve into the lumen.

* * * * *